US00PP19842P3

(12) United States Plant Patent
Rullo

(10) Patent No.: US PP19,842 P3
(45) Date of Patent: Mar. 24, 2009

(54) PLUM×CHERRY INTERSPECIFIC HYBRID TREE NAMED 'NADIA'

(50) Latin Name: *Prunus salicina×Prunum avium*
Varietal Denomination: Nadia

(75) Inventor: Joseph Rullo, Shepparton (AU)

(73) Assignee: Cherry Royale Pty Ltd, Bathurst, New South Wales (AU)

( * ) Notice: Subject to any disclaimer, the term of this patent is extended or adjusted under 35 U.S.C. 154(b) by 0 days.

(21) Appl. No.: 11/891,041

(22) Filed: Aug. 7, 2007

(65) Prior Publication Data

US 2009/0044301 P1 Feb. 12, 2009

(51) Int. Cl.
*A01H 5/00* (2006.01)

(52) U.S. Cl. ..... Plt./180
(58) Field of Classification Search ..... Plt./180
See application file for complete search history.

(56) References Cited

PUBLICATIONS

UPOV ROM GTITM Computer Database, GTI Jouve Retrieval Software 2008/02 Citation for 'Nadia'.*

* cited by examiner

*Primary Examiner*—Wendy C. Haas
(74) *Attorney, Agent, or Firm*—Stratton Ballew PLLC

(57) ABSTRACT

A plum×cherry interspecific hybrid tree named 'Nadia.' The new selection is the result of a controlled cross of 'Black Amber' plum and 'Supreme' cherry, and is notable for its sweet, red fruit.

4 Drawing Sheets

Latin name of the genus and species of the plant claimed: *Prunus salicina×Prunus avium.*
Variety denomination: 'Nadia'.

BRIEF DESCRIPTION OF THE VARIETY

'Nadia' is a new interspecific hybrid resulting from a controlled cross of 'Black Amber' plum (not patented) and 'Supreme' cherry (not patented). The inventor hand pollinated a limb of a 'Black Amber' plum tree located in his commercial orchard at Shepparton, Victoria, New South Wales, Australia, with pollen from 'Supreme' cherry. After pollination, the limb was bagged to prevent further pollination. Two hundred seeds were collected from fruit set on the selected branch, and planted in pots for observation. Of the two hundred seeds planted, only 5 produced seedlings. The five seedlings were grown on until large enough to harvest budwood for further propagations. The budwood was topworked by grafting onto 20 plum rootstock trees for evaluation. It was from these topworked trees that 'Nadia' was selected. Since the initial selection, four generations of asexual propagation have been carried out. It has been observed that the traits identified in the original selection have been carried forward and remain stable and true to type in the asexually propagated trees of 'Nadia'.

BRIEF DESCRIPTION OF THE PHOTOGRAPHS

DETAILED BOTANICAL DESCRIPTION OF THE VARIETY

Figure 1:
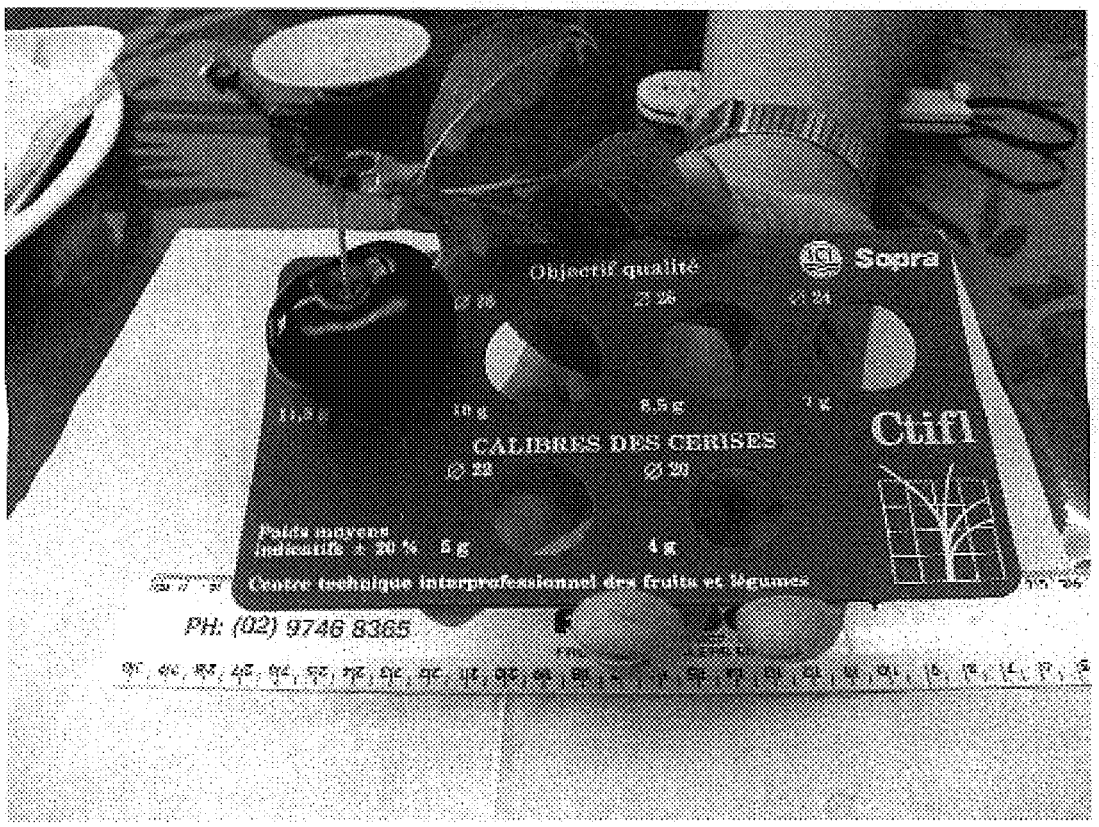
FIG. 1 shows the fruit of 'Nadia' with reference to a standard cherry sizing card.
Figure 2:
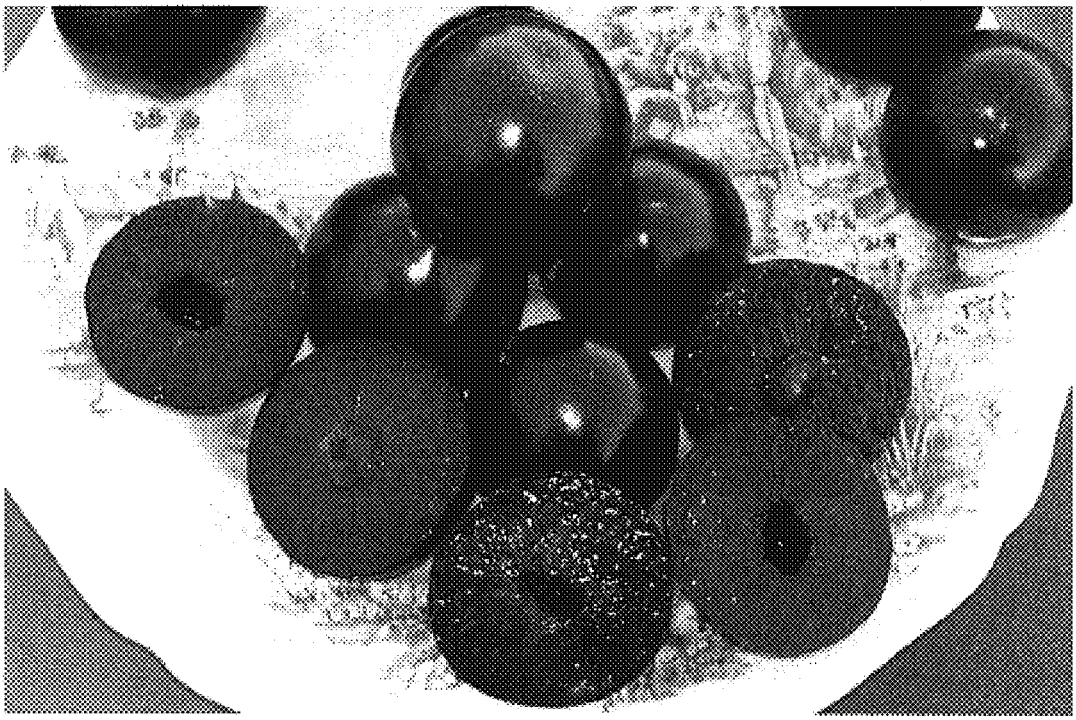
FIG. 2 shows whole and sectioned fruit of 'Nadia'.
Figure 3:
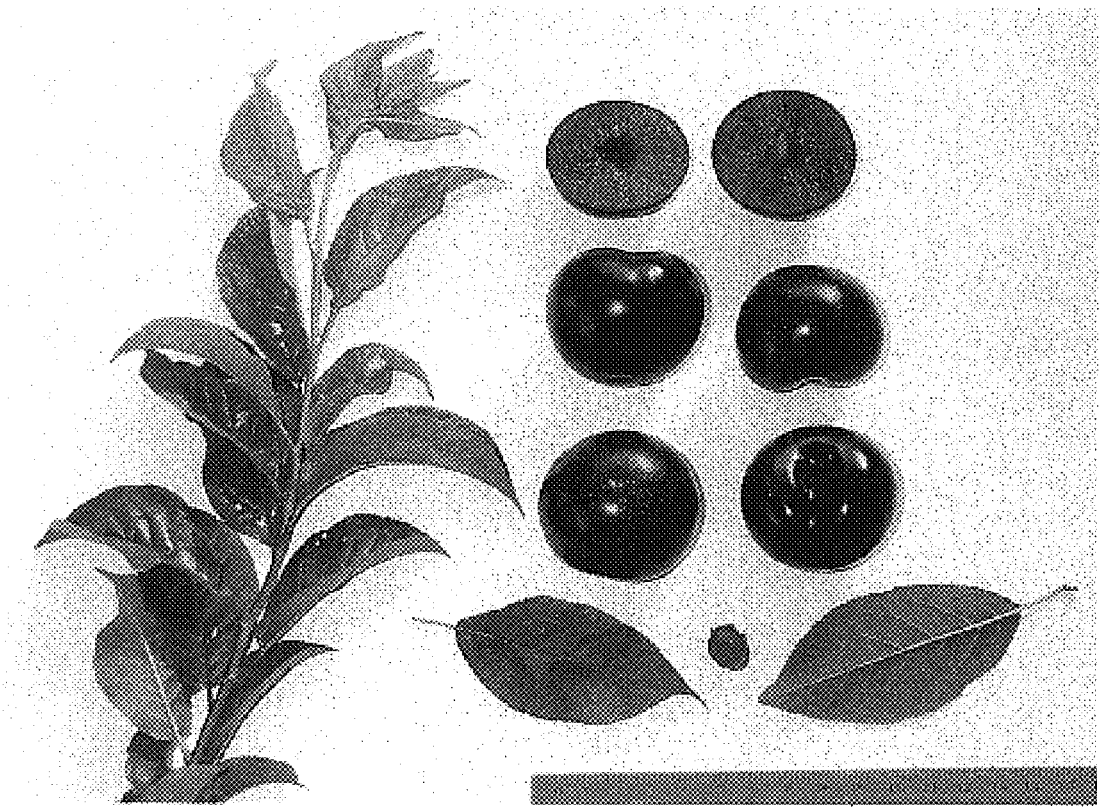
FIG. 3 shows the fruit and leaves of 'Nadia'.
Figure 4:
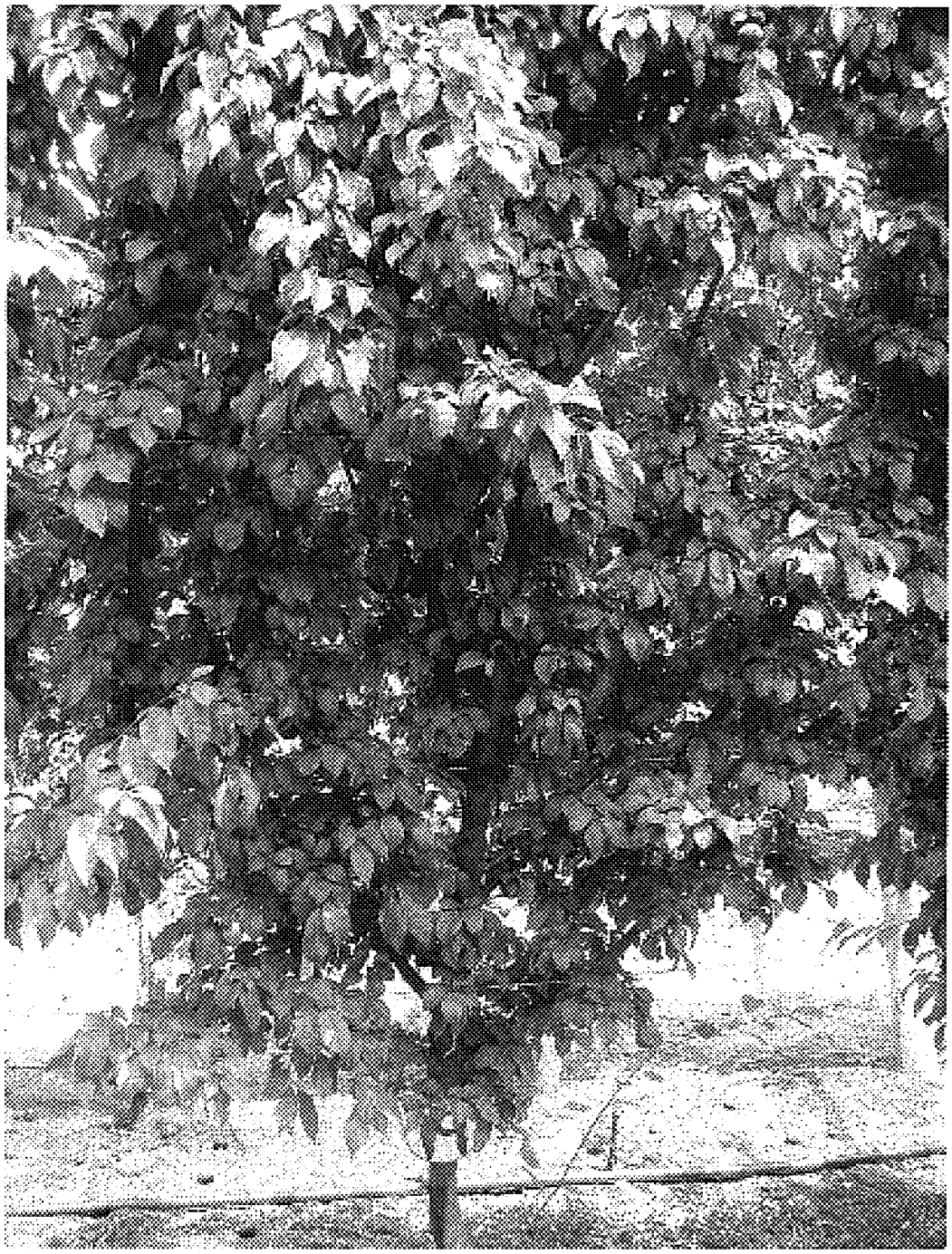
FIG. 4 shows a tree of the 'Nadia' variety.

The following is a detailed botanical description of the new plum×cherry interspecific hybrid tree 'Nadia', based on observations made during the 2005 growing season at Shepparton, Victoria, New South Wales, Australia, and further based on observations of 2 year old trees made during the 2006/2007 growing season at Manjimup, Western Australia It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Size.*—3 to 4 m high; 2 m wide.
*Vigor.*—Medium to strong; 75 cm per year.
*Habit.*—Semi-upright.
*Canopy density.*—Dense.
*Branching.*—Strong.
*Trunk.*—Diameter 3 cm at 30 cm above soil level; bark texture smooth; bark color greyed orange 172A. Lenticels — length 3 to 5 mm, greyed orange 164B, density 6 to 8 per $cm^2$ Production — more than 30 tonnes/hectare.

One year old shoot:

*Attitude.*—Erect to semi-erect.
*Number of lenticels.*—Medium.
*Position of bud in relation to shoot.*—Slightly held out.
*Anthocyanin coloration of tip of young shoot.*—Medium.

Branch:

*Size.*—Representative branch 1.5 cm diameter at 50 cm above the ground

*Crotch angle of bearing branches.*—0 to 90° from vertical.

*Texture.*—Smooth.

*Color.*—First year wood greyed orange 174A; second year wood greyed orange 177A.

*Lenticels.*—Length 1 mm, greyed orange 164B, density 3 to 4 per $cm^2$.

Leaf: Measurements are from mature leaves attached at midpoint of actively growing upright shoots of current season's growth.

*Length.*—Medium to long, 9 cm.

*Width.*—Medium, 5 cm.

*Ratio length to width.*—Medium to large.

*Shape.*—Elliptic.

*Shape of tip.*—Pointed.

*Margin.*—Crenate.

*Attitude.*—Horizontal to downwards.

*Color.*—Upper side — light green 141A, glossy.

*Color.*—Lower side — light green 143A.

*Midvein.*—Width 0.5 mm; upper surface green 136A; lower surface green 136A.

*Pubescence of lower surface.*—Weak.

*Petiole.*—Short to medium, length 1 cm, width 4 mm; green 140B.

*Nectaries.*—Present, orange yellow.

Flower:

*Buds.*8–10 per spur, length 5 mm, width 2 mm; pedicel length 1 cm.

*Diameter of corolla.*—Medium to large.

*Petal shape.*—Broad elliptic to obovate.

*Petal size.*—Medium.

*Relative position of petal margins.*—Free.

*Undulation of margin.*—Weak.

*Sepal shape.*—Elliptic.

*Bloom time.*—First bloom 25 July, full bloom 8 August at Manjimup, Western Australia.

Fruit:

Size. —Diameter 42 to 48 mm, large to very large as compared to 'Cherry Supreme' cherry, small as compared to 'Black Amber' plum; weight 60 g.

*Shape.*—Cordate.

*Shape of pistil end.*—Pointed.

*Depth of stalk cavity.*—Very shallow.

*Position of maximum diameter.*—Toward stalk end.

*Symmetry.*—Symmetric.

*Depth of suture.*—2 mm.

*Cavity.*—Very shallow, 5 mm; diameter 10 mm shoulder to shoulder.

*Color of skin.*—Dark red to purple 59A.

*Thickness of skin.*—Medium.

*Tendency to crack.*—None.

*Size of lenticels on skin.*—Very small.

*Number of lenticels on skin.*—Very few.

*Color of juice.*—Red.

*Color of flesh.*—Dark red 57B.

*Texture of flesh.*—Melting.

*Firmness.*—Firm to very firm.

*Acidity.*—Very low.

*Sweetness.*—High to very high, 20–24° Brix.

*Juiciness.*—Strong.

*Length of stalk.*—Medium, 2 cm.

*Abcission layer between stalk and fruit.*—Present.

*Thickness of stalk.*—Medium, 2 mm.

*Stalk color.*—Green 140B.

*Adherence of stone to flesh.*—Semi-adherent.

*Fruit keeping quality.*—Excellent, 7 to 10 days at room temperature.

*Fruit shipping quality.*—Excellent.

*Time of fruit maturity.*—Medium, eating ripe early January at Shepparton, Victoria, Australia (2005/2006 growing season). First picking 5 January, last picking 10 January.

Stone:

*Size.*—Very small, length 1 cm, width 1 cm.

*Shape in profile.*—Round to round-elliptical.

*Shape in ventral view.*—Globular.

*Shape in basal view.*—Round.

*Symmetry.*—Symmetric.

*Position of maximum width.*—At center.

*Size relative to fruit.*—Very small.

*Color.*—Greyed yellow 162D.

*Texture of lateral surfaces.*—Fine grained.

*Margins of dorsal groove.*—Broken.

*Sharpness of edges.*—Very weak.

*Width of ventral zone.*—Medium.

*Width of stalk end.*—Medium.

It is claimed:

1. A new and distinct plum×cherry interspecific hybrid tree, substantially as described and illustrated herein.

* * * * *